(12) United States Patent
Radisson et al.

(10) Patent No.: US 9,757,318 B2
(45) Date of Patent: *Sep. 12, 2017

(54) PROCESS FOR RELAXING KERATIN FIBRES

(75) Inventors: Xavier Radisson, Asnieres sur Seine (FR); Philippe Barbarat, Bois-Colombes (FR); Gerard Malle, Villiers S/Morin (FR); Stephane Diridollou, Chicago, IL (US)

(73) Assignee: L'OREAL, Paris (FR)

( * ) Notice: Subject to any disclaimer, the term of this patent is extended or adjusted under 35 U.S.C. 154(b) by 1588 days.

This patent is subject to a terminal disclaimer.

(21) Appl. No.: 12/841,482

(22) Filed: Jul. 22, 2010

(65) Prior Publication Data

US 2010/0284954 A1 Nov. 11, 2010

Related U.S. Application Data

(63) Continuation of application No. 11/287,292, filed on Nov. 28, 2005, now abandoned.

(60) Provisional application No. 60/646,616, filed on Jan. 26, 2005.

(30) Foreign Application Priority Data

Nov. 26, 2004 (FR) ...................... 04 52775

(51) Int. Cl.
*A61Q 5/04* (2006.01)
*A61K 8/43* (2006.01)
*A61K 8/49* (2006.01)
*A61K 8/42* (2006.01)

(52) U.S. Cl.
CPC ................. *A61K 8/43* (2013.01); *A61K 8/42* (2013.01); *A61K 8/49* (2013.01); *A61Q 5/04* (2013.01)

(58) Field of Classification Search
CPC .............. A61Q 5/04; A61K 8/42; A61K 8/49
USPC ....................................................... 424/70.2
See application file for complete search history.

(56) References Cited

U.S. PATENT DOCUMENTS 1,861,040 A * 5/1932 Williams ...................... 132/118

FOREIGN PATENT DOCUMENTS

| EP | 0 100 901 | | 2/1984 |
|---|---|---|---|
| EP | 0167866 A2 | * | 1/1986 |
| EP | 0190834 A2 | * | 8/1986 |
| EP | 1 468 667 | | 10/2004 |
| EP | 1 532 963 | | 5/2005 |
| EP | 1 535 598 | | 6/2005 |
| GB | 1 466622 | | 3/1977 |
| JP | 2002356408 | * | 12/2002 |

OTHER PUBLICATIONS

McMullen et al. "Thermal degradation of Hair, I. Effect of curling ions" J. Cosmet. Sci. 1998, vol. 49, pp. 223-244.*
European Search Report as received in the corresponding European Patent Application No. EP14180383.3 dated Nov. 21, 2014.
Database CAPLUS [Online] Chemical Abstracts Service, Columbus, Ohio, US; Kobayashi, Mikio et al.: "hair straightening or wave-setting compositions containing protein denaturants", XP002338918, extrait de CAPLUS, Database accession No. 2003-585180 & JP 2003 212737 A (Hoyu Co Ltd) Jul. 30, 2003.
Database EPODOC [Online] European Patent Office, The Hague, NL; Jan. 20, 1998, Kajino Takayoshi et al., "Hair treatment agent composition", XP0022732716, Database accession No. JP-17653196-A & JP H10 17441 A (Kao Corp) Jan. 20, 1998.
R. McMullen, et al., "Thermal degradation of 1-9 hair. I. Effect of curling irons", J. Cosmet. Sci., vol. 49, Jul. 1, 1998, pp. 223-244.

\* cited by examiner

*Primary Examiner* — Shengjun Wang
(74) *Attorney, Agent, or Firm* — Oblon, McClelland, Maier & Neustadt, L.L.P.

(57) ABSTRACT

The invention relates to a process for relaxing keratin fibers by applying to the keratin fibers a relaxing composition containing at least one denaturing agent with a molecular mass of greater than 18.1 g/mol, present in a molar concentration of between 1M and 8M, and raising the temperature of the keratin fibers to a temperature of between 110 and 250° C.

18 Claims, No Drawings

PROCESS FOR RELAXING KERATIN FIBRES

REFERENCE TO PRIOR APPLICATIONS

This application claims priority to U.S. provisional application 60/646,616 filed Jan. 26, 2005, and to French patent application 0452775 filed Nov. 26, 2004, both incorporated herein by reference.

FIELD OF THE INVENTION

The invention relates to a process for relaxing keratin fibres with heat and at least one denaturing agent.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Two techniques are used to obtain permanent reshaping of the hair. They are based on cleavage of the disulfide covalent bonds present in keratin (cystine):

- the first consists, in a first stage, in performing this opening of the disulfide bonds using a composition containing a reducing agent, and then after, preferably, having rinsed the hair, in reconstituting, in a second stage, the said disulfide bonds by applying to the hair, that has been placed under tension beforehand by means of rollers or the like or shaped or smoothed out by other means, an oxidizing composition also known as a fixer, so as to give the head of hair the desired shape. This technique makes it possible either to make the hair wavy or to relax it, uncurl it or smooth it out;
- the second consists in performing a "lanthionization" operation, using a composition containing a base belonging to the hydroxide family. It leads to the replacement of the disulfide bonds (—CH2-S—S—CH2-) with lanthionine bonds (—CH2-S—CH2-). This lanthionization operation involves two consecutive chemical reactions:

The first reaction consists of a beta-elimination on cystine brought about by a hydroxide ion, leading to the cleavage of this bond and to the formation of dehydroalanine.

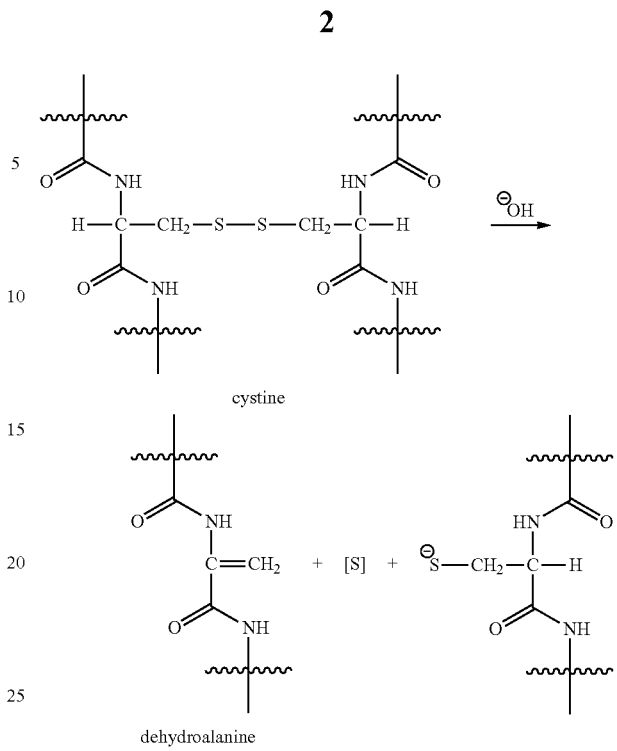

The second reaction is a reaction of the dehydroalanine with a thiol group. Specifically, the double bond of the dehydroalanine formed is a reactive double bond. It can react with the thiol group of the cysteine residue that has been released to form a new bond known as a lanthionine bridge or bond or residue.

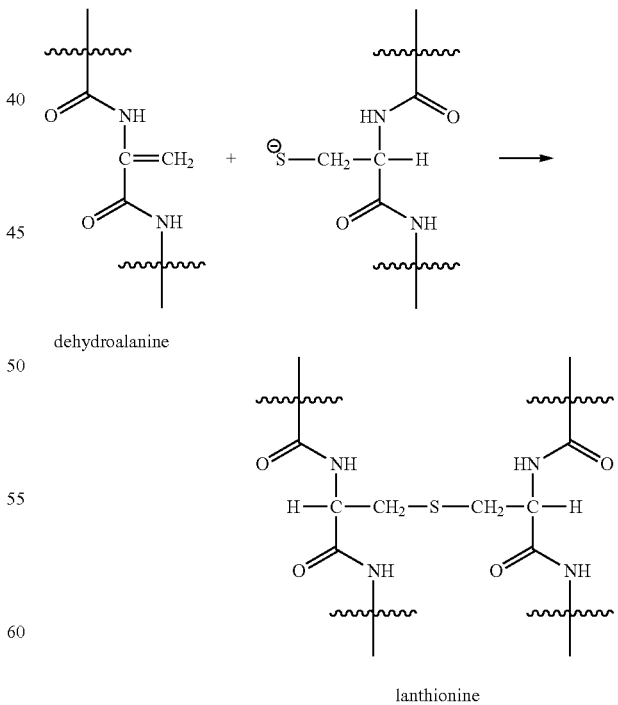

Relative to the first technique using a reducing agent, this lanthionization technique does not require a fixing step, since the formation of the lanthionine bridges is irreversible.

It is thus performed in a single step and makes it possible either to make the hair wavy or to relax it, uncurl it or smooth it out. However, it is mainly used for relaxing naturally frizzy hair.

For the first technique, the reducing compositions generally used for the first step of a permanent-waving or relaxing operation contain thiols, sulfites or bisulfites as reducing agent. These agents are generally used in essentially aqueous medium at concentrations of between 0.5 and 1M to obtain good opening of the disulfide bonds. Among the thiols, those commonly used are thioglycolic acid, cysteamine, glyceryl monothioglycolate, thiolactic acid and cysteine. Thioglycolic acid is particularly effective for reducing the disulfide bonds of keratin at alkaline pH, especially in the form of ammonium thioglycolate, and is the product most widely used in permanent-waving ("hair waving"). However, it has been found that thioglycolic acid must be used in a sufficiently basic medium (in practice at a pH of between 8.5 and 9.5) if it is desired to obtain curliness of satisfactory intensity. Besides the drawback of giving off an unpleasant odour requiring the use of more or less efficient fragrances to mask the odours, the use of a thiol at alkaline pH also leads to degradation of the fibre and most particularly to impairment of artificial colorations.

Sulfites or bisulfites are mainly used for relaxing. They have similar drawbacks to thiols, with less efficacy.

Thiols and sulfites (or bisulfites) also have the drawback of having poor stability in aqueous solution.

In general, the durability of the reshaping effects obtained with thiols and sulfites by reduction of disulfides followed by fixing is judged to be very much inferior to that which may be obtained via the lanthionization technique.

For the second technique, the compositions generally used to perform the lanthionization contain as base a hydroxide such as sodium hydroxide, guanidinium hydroxide or lithium hydroxide. These lanthionization active agents, which allow the disulfide bonds to be opened via a beta-elimination mechanism, are generally used as a water-oil emulsion at concentrations of between 0.4 and 0.6M, by leaving them to act generally for 10 to 15 minutes at room temperature. Sodium hydroxide remains the agent most widely used. Guanidinium hydroxide is now the preferred compound for many compositions. These two hydroxides, sodium hydroxide and guanidinium hydroxide, are the two main agents used for relaxing or uncurling naturally frizzy hair. They have several advantages over ammonium thioglycolate and sulfites, in particular an absence of unpleasant odour, the fact that only one implementation step is required (shorter treatment time), and a much greater durability and efficacy of the reshaping of the hair.

However, these hydroxides have the major drawback of being caustic. This causticity affects the scalp by causing irritation, which may occasionally be severe. This may partially be remedied by first applying to the scalp a fatty protective cream often referred to as a "base" or "base cream", the word "base" in this instance not having the meaning of a basic agent in the chemical sense. When the protective cream is combined with hydroxide in a single composition, it is generally known as a "no-base" cream, as opposed to the above name. This "no-base" technology is preferred.

The causticity of hydroxides also affects the condition of the hair by firstly giving it a coarse feel and secondly making it much more fragile, this fragility possibly going as far as flaking or even breaking, or even the dissolution of the hair if the treatment is prolonged. In certain cases, hydroxides also cause decolorization of the natural colour of the hair.

Formulations containing sodium hydroxide are generally known as "lye relaxers" and those not containing it are known as "no-lye relaxers".

The main "no-lye" relaxing formulations use guanidinium hydroxide. Since guanidinium hydroxide is unstable, it is generated extemporaneously by mixing guanidine carbonate and a source of very sparingly soluble hydroxide such as calcium hydroxide. The reaction between these two compounds leads to the formation of guanidinium hydroxide and calcium carbonate, which precipitates in the composition. The presence of this precipitate makes the final rinsing of the hair much more difficult and leaves on the hair and the scalp mineral particles that give it a coarse feel and an unattractive appearance resembling dandruff. The recent success of guanidinium hydroxide ("no-lye") in the face of sodium hydroxide ("lye") appears to arise from better relaxing efficacy and better skin tolerance. However, these technologies using bases of the hydroxide family remain very aggressive for the hair and the scalp and require very strict control of the application time to avoid excessive irritation and impairment of the hair, which may go as far as breaking of the hair. This aggressiveness arising from the causticity of hydroxides is just reason for these hair lanthionization compositions not being used for permanent-waving ("hair waving"), but being reserved for relaxing ("hair straightening" or "hair relaxing").

Furthermore, hydroxides are known to be good agents for hydrolysing amide functions (cf. for example March's Advanced Organic Chemistry, 5 ed., Wiley Interscience, New York, "Hydrolysis of Amides" pages 474 et seq.), which thus lead to cleavage of the peptide bonds via direct nucleophilic attack. It is thus probable that the impairments observed on the hair and keratin materials in the broad sense are largely due to partial hydrolysis of the amide bonds of keratin.

There is thus a real need for relaxing compositions that are markedly less aggressive to the hair.

Various studies have been conducted in order to overcome the drawbacks of both reducing agents (first technique) and/or of hydroxides (second technique).

Thus, to replace thioglycolic acid, numerous reducing agents have been proposed, but thioglycolic acid in its ammonium thioglycolate form remains both the compound of reference and the compound most widely used in cosmetic formulations, both for shaping and for straightening.

It has also been proposed in numerous patents to combine common reducing agents (thiols, sulfites or bisulfites) with urea or alkylureas to reduce the irritation and damage caused on the hair both by shaping and by relaxing. Reference will be made, for example, to:
  patent application CA 1315204, which describes a composition containing ammonium thioglycolate (5.5-11.5%) and urea or a monoalkylurea (1-3%) for shaping the hair,
  U.S. Pat. No. 3,847,165, which describes a composition containing ammonium thioglycolate (1.2-1.4M) and urea (2.0-2.7M) for shaping the hair at acidic pH,
  patent application NL 6 410 355, which describes a composition containing a sulfite (0.8-1.5M) and urea (0.6-3.0M) for shaping and relaxing the hair,
  patent application JP 2000/229 819, which describes a composition containing a sulfite or bisulfite (0.5-15%), urea (0.5-15%) and an alcohol (ethanol and/or isopropanol, 1-30%) for shaping and relaxing the hair.

It has also been proposed in numerous patents to combine hydroxides, serving as lanthionization active agent, with certain additives generally serving to protect the hair. Mention will be made, for example, of:

patent application WO 2002/003 937, which describes a composition containing C3-C5 monosaccharides, patent application WO 2001/064 171, which describes a composition containing complexing agents, U.S. Pat. No. 5,641,477, which describes a composition containing a hydrogenated starch hydrolysate, patent application WO 02/085 317, which describes a composition containing organic nucleophiles, which react during the second step with the dehydroalanine formed with hydroxides, to give new bridges.

Although all these proposals lead to more or less marked improvements, they do not make it possible to significantly reduce the damage caused by the causticity itself of hydroxides.

As indicated above, the use of reducing agents leads to mediocre durability for relaxing or uncurling, and the use of hydroxides, on account of their causticity, limits their use to the field of relaxing.

SUMMARY OF THE INVENTION

After extensive studies, it has now been discovered, entirely surprisingly and unexpectedly, that the hair can be durably relaxed by combining the action of a denaturing agent and by heating to a temperature above 110° C. Excellent results in terms of relaxing, hair cosmetic properties and fibre integrity are thus obtained.

Definitions

According to the invention, the term "keratin fibres" means fibres of human or animal origin such as head hair, body hair, the eyelashes, wool, angora, cashmere or fur. Although the invention is not limited to particular keratin fibres, reference will nevertheless be made more particularly to head hair.

According to the invention, the term "relaxing" covers the relaxing, straightening or uncurling, and includes such effects on, e.g., Caucasian and African hair. According to the invention, the term "to relax" means to relax, to straighten or to uncurl.

The term "denaturing agent" includes those compounds specifically identified as such herein and means an organic or mineral compound containing both at least one electron-donating site of basic or nucleophilic nature and at least one electron-withdrawing site of acidic or electrophilic nature, which interact with the weak bonds of keratin.

According to the invention, a denaturing agent is a compound capable of reducing the optical rotation of a model protein, for instance bovine serum albumin, by at least 7° and/or 5° at 579 nm, the measurements being taken after 3 hours of incubation at 37° C., using a polarimeter, as described in Biochemistry 2 (1), 47-57, 1963:

either in 0.05M pH 7.6 TRIS buffer, or in a 5.45M urea solution when the solubility of the compound is insufficient in 0.05M pH 7.6 TRIS buffer.

The compound is considered as being a denaturing agent according to the invention if the reduction in the optical rotation is at least 7° in 0.05M pH 7.6 TRIS buffer and/or at least 5° in 5.45M urea solution.

The term "weak bonds of keratin" means all of the non-covalent bonds, such as:

the saline bonds resulting from coulombic interactions between the functional groups present on the side chains of amino acids, hydrogen bonds, which are established between the amino acids especially via oxygen and hydrogen atoms, hydrophobic bonds resulting from the tendency of the non-polar chains of amino acids to associate in order to minimize the contacts with water.

The term "heating means" is a term invoking 35 U.S.C. 112, paragraph 6, and is defined as any means for heating keratin fibres to a temperature of at least 110° C., such as heating irons, for example flat or round irons, microwave generators, sources of infrared radiation, etc. The terms "heater" and "heaters" include all of these examples but are not terms implicating 35 U.S.C. 112, paragraph 6.

DETAILED DESCRIPTION OF THE PREFERRED EMBODIMENTS

Without being bound by theory, the inventor believes that there is a combined action, on the keratin fibres, of a denaturing agent and of the action of a heater or a heating means, which allows the fibres to be effectively and durably relaxed.

The Inventor has found that it is possible to overcome the drawbacks of the prior art and to meet the abovementioned objectives by performing a process for relaxing keratin fibres comprising:

applying to the keratin fibres a relaxing composition comprising at least one denaturing agent preferably having a molecular mass (weight) of greater than 18.1 g/mol, present in a molar concentration of between 1M and 8M in said composition, and raising the temperature of the keratin fibres, for example using a heater or heating means, to a temperature of between 110 and 250° C.

These two steps can be accomplished in any order, or simultaneously. Preferably, they are accomplished in the order stated above.

A molar concentration of between 1M and 8M generally corresponds to a weight concentration of between about 6% and about 80% relative to the total weight of the composition.

Thus, one subject of the invention is a process for relaxing keratin fibres comprising:

applying to the keratin fibres a relaxing composition comprising at least one denaturing agent with a molecular mass of greater than 18.1 g/mol, present in a molar concentration of between 1M and 8M, then raising the temperature of the (treated) keratin fibres, using a heater or heating means, to a temperature of between 110 and 250° C.

Optionally, the hair can be dried to some extent after treatment with the relaxing composition prior to application of heat to raise the temperature of the keratin fibres, for example by wiping with a towel, etc. However, it is preferred that the hair have remaining thereon at least some denaturing agent when heat is applied so as to obtain the benefits of the present invention.

Preferably, the relaxing composition comprises between 2M and 8M of the said denaturing agent; this corresponds to a weight concentration of between about 12% and about 80%, relative to the total weight of the composition, of the said denaturing agent.

Advantageously, the temperature is raised using a heater or by heating means to a temperature of between 120° C. and 220° C. and more advantageously between 140° C. and 220° C.

Advantageously, the molar mass of the denaturing agent is between 40 and 600 g/mol.

Preferably, the relaxing composition is applied to wet keratin fibres.

As noted above, the removal of excess relaxing composition, for example using a towel, may advantageously be inserted between the act of applying the relaxing composition and the act of raising the temperature.

Preferably, the denaturing agent is chosen from protein-denaturing agents such as ureas, guanidines, amidines, urethanes, aromatic monohydroxylated, dihydroxylated, trihydroxylated or polyhydroxylated derivatives, nitrogen heterocycles of the imidazole or triazole family, carboxylic acids and amide and thioamide derivatives thereof, thioureas, amino acids, alcohols, polyols, amine oxides, surfactants containing sugar, choline, deoxycholine or polyethylene glycol units, metal salts and sulfamides.

The denaturing agent is advantageously a urea or a guanidine.

As "urea" that may be used as relaxing active agent, this term refers to any derivative comprising in its chemical formula a carbonyl group simply bonded to 2 nitrogen atoms. These ureas are more particularly selected from the compounds of general formulae (I) and (II) below:

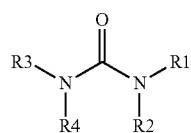

(I)

in which:
R1, R2, R3 and R4 represent, independently:
(i) a hydrogen atom, or
(ii) a linear or branched lower C1-C4 alkyl or alkenyl radical, optionally substituted with a radical chosen from: hydroxyl, amino, dimethylamino, carboxyl or carboxamide or N-methylcarboxamide.

When R1, R2 and R3 represent a hydrogen atom, R4 may also denote a radical chosen from the following: carboxamide; methoxy; ethoxy; 1,2,4-triazolyl; cyclopentyl; methoxycarbonyl; ethoxycarbonyl; CO—CH═CH—COOH; phenyl optionally substituted with a chlorine atom or a hydroxyl radical; benzyl; or 2,5-dioxo-4-imidazolidinyl.

When R1 and R3 represent a hydrogen atom, R2 may also represent a hydrogen atom or a methyl or ethyl radical and R4 an acetyl radical.

When R1═R2═H, R3 and R4 may also form, with the nitrogen atom that bears them, a piperidine or 3-methylpyrazole or 3,5-dimethylpyrazole or maleimide ring.

Finally, R1 and R2, and also R3 and R4, may also form, with the nitrogen atom that bears them, an imidazole ring.

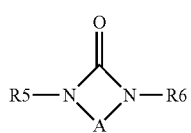

(II)

in which:
R5 and R6 represent, independently of each other:
(i) a hydrogen atom, or
(ii) a linear or branched C1-C4 lower alkyl radical, optionally substituted with a radical chosen from: hydroxyl, amino, dimethylamino, carboxyl or carboxamide, and A represents the radicals: CH2-CH2 or CH═CH or CH2-CO or CO—NH or CH═N or CO—CO or CHOH—CHOH or (HOOC)CH—CH or CHOH—CO or CH2-CH2-CH2 or CH2-NH—CO or CH═C(CH3)-CO or NH—CO—NH or CH2-CH2-CO or CH2-N(CH3)-CH2 or NH—CH2-NH or CO—CH(CH3)-CH2 or CO—CH2-CO or CO—NH—CO or CO—CH(COOH)—CH2 or CO—CH═C(COOH) or CO—CH═C(CH3) or CO—C(NH2)═CH or CO—C(CH3)═N or CO—CH═CH or CO—CH═N or CO—N═CH.

Among the compounds of formula (I), mention may be made especially of the following preferred compounds:
urea
methylurea
ethylurea
propylurea
isopropylurea
n-butylurea
sec-butylurea
isobutylurea
tert-butylurea
cyclopentylurea
1-ethoxyurea
2-hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleimide
biuret
N-carbamoylmaleamic acid
1-piperidinecarboxamide
1,2,4-triazol-4-ylurea
hydantoic acid
methyl allophanate
ethyl allophanate
acetylurea
2-hydroxyethyleneurea
2-(hydroxyethyl)ethyleneurea
N-allyl-N'-ethylurea
diallylurea
2-chloroethylurea
N,N-dimethylurea
N,N-diethylurea
N,N-dipropylurea
1-cyclopentyl-1-methylurea
1,3-dimethylurea
1,3-diethylurea
1,3-bis(2-hydroxyethyl)urea
1,3-bis(2-hydroxypropyl)urea
1,3-bis(3-hydroxypropyl)urea
1,3-dipropylurea
1-ethyl-3-propylurea
1-sec-butyl-3-methylurea
1-isobutyl-3-methylurea
1-cyclopentyl-3-methylurea
N-acetyl-N'-methylurea
trimethylurea
1-butyl-3,3-dimethylurea
tetramethylurea
benzylurea Among the compounds of formula (II), mention may be made especially of the following preferred compounds:
parabanic acid
1,2-dihydro-3-H-1,2,4-triazol-2-one
barbituric acid
uracil
1-methyluracil
3-methyluracil
5-methyluracil
1,3-dimethyluracil
5-azauracil
6-azauracil
5-fluorouracil
6-fluorouracil
1,3-dimethyl-5-fluorouracil
5-aminouracil
6-aminouracil
6-amino-1-methyluracil
6-amino-1,3-dimethyluracil
4-chlorouracil
5-chlorouracil
5,6-dihydrouracil
5,6-dihydro-5-methyluracil
2-imidazolidone hydrate
1-methyl-2-imidazolidinone
1,3-dimethyl-2-imidazolidinone
4,5-dihydroxyimidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydantoin
5-n-propylhydantoin
5-ethyl-5-methylhydantoin
5-hydroxy-5-methylhydantoin
5-hydroxymethylhydantoin
1-allylhydantoin
1-aminohydantoin
hydantoin 5-acetic acid
4-amino-1,2,4-triazolone-3,5-dione
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
barbituric acid
1,3-dimethylbarbituric acid
cyanuric acid
1-methylhexahydropyrimidine-2,4-dione
1,3-dimethyl-3,4,5,6-tetrahydro-2-1H-pyrimidinone
5-(hydroxymethyl-2,4-(1H,3H)-pyrimidinedione
2,4-dihydroxypyrimidine-5-carboxylic acid
6-azathymine
5-methyl-1,3,5-triazinan-2-one
N-carbamoylmaleamic acid
alloxan monohydrate Among the compounds of formula (I) that may especially be mentioned are the following particularly preferred compounds:
urea
methylurea
ethylurea
propylurea
1-ethoxyurea
2-hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
N-carbamoylmaleimide
N-carbamoylmaleamic acid
1-piperidinecarboxamide
1,2,4-triazol-4-ylurea
hydantoic acid
acetylurea
2-hydroxyethyleneurea
2-(hydroxyethyl)ethyleneurea
N-allyl-N'-ethylurea
diallylurea
2-chloroethylurea
N,N-dimethylurea
1,3-dimethylurea
1,3-diethylurea
1,3-bis(2-hydroxyethyl)urea
1,3-dipropylurea
1-ethyl-3-propylurea
N-acetyl-N'-methylurea
benzylurea Among the compounds of formula (II) that may especially be mentioned are the following particularly preferred compounds:
1,2-dihydro-3H-1,2,4-triazol-2-one
uracil
1-methyl-2-imidazolidinone
1,3-dimethyl-2-imidazolidinone
4,5-dihydroxyimidazolidin-2-one
1-(2-hydroxyethyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
hydantoin
5-hydroxymethylhydantoin
hydantoin 5-acetic acid
urazole
orotic acid
dihydroxyorotic acid
2,4,5-trihydroxypyrimidine
4,5-diamino-2,6-dihydroxypyrimidine
2,4-dihydroxypyrimidine-5-carboxylic acid
5-methyl-1,3,5-triazinan-2-one
1,3-dimethyl-3,4,5,6-tetrahydro-2-1H-pyrimidinone
N-carbamoylmaleamic acid
alloxan monohydrate As "guanidine" that may be used as relaxing active agent, this term means any derivative comprising in its chemical formula at least one carbon atom doubly bonded to a nitrogen atom and singly bonded to two other nitrogen atoms. These guanidines are more particularly selected from the compounds of general formula (III) below:

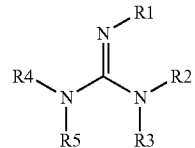

(III)

in which:

R1, R2, R3, R4 and R5 represent, independently:
(iii) a hydrogen atom, or
(iv) a linear or branched C1-C4 lower alkyl or alkenyl radical, optionally substituted with one or two radicals chosen from: hydroxyl, amino, dimethylamino, methoxy, ethoxy, carboxyl, carboxamide, N-methylcarboxamide or $SO_3H$ When R1, R2, R3 and R4 represent a hydrogen atom, R5 may also denote a radical chosen from the following: acetyl; chloroacetyl; carboxamide; methoxy; ethoxy; 1,2,4-triazolyl; cyclopentyl; methoxycarbonyl; ethoxycarbonyl; CO—CH═CH—COOH; phenyl optionally substituted with a chlorine atom or a hydroxyl radical; benzyl; thiazolidone; benzimidazole; benzoxazole; benzothiazole; or C(═NH)—NR6R7 in which R6 and R7 denote, independently of each other, a hydrogen atom or a linear or branched C1-C4 lower alkyl radical, optionally substituted with one or two radicals chosen from: hydroxyl, amino, dimethylamino, carboxyl and carboxamide; or N-methylcarboxamide; or alternatively a phenyl radical.

When R1=R2=R3=H, R4 and R5 may also form, with the nitrogen atom that bears them, a pyrrolidine, piperidine, pyrazole or 1,2,4-triazole ring, optionally substituted with one or two radicals chosen from: hydroxyl, amino and carboxyl.

When R1=R2=H, and R4=H or methyl, R3 and R5 may also together form a 5-membered ring optionally containing an oxo group
and the organic or mineral salts thereof.

Among the compounds of formula (III) that may especially be mentioned are the following preferred compounds:
guanidine hydrochloride
guanidine acetate
guanidine sulfate
guanidine carbonate
guanidine bicarbonate
guanidine phosphate
guanidine sulfamate
aminoguanidine
aminoguanidine hydrochloride
aminoguanidine sulfate
aminoguanidine bicarbonate
1,3-diaminoguanidine hydrochloride
1-acetylguanidine
chloroacetylguanidine hydrochloride
guanylurea
guanylurea phosphate
phenylguanidine carbonate
phenylguanidine bicarbonate
1-methylguanidine hydrochloride
1,1-dimethylguanidine hydrochloride
1-ethylguanidine hydrochloride
1,1-diethylguanidine hydrochloride
creatine
creatine monohydrate
creatinine hydrochloride
agmatine
agmatine sulfate
guanidinoacetic acid
guanidinosuccinic acid
3-guanidinopropionic acid
4-guanidinobutyric acid
5-guanidinovaleric acid
beta-N-methylguanidinopropionic acid
N-methylguanidinopropionic acid
N-(2-hydroxyethyl)guanidine
N-(3-hydroxypropyl)guanidine
biguanide hydrochloride
N-methylbiguanide hydrochloride
N-ethylbiguanide hydrochloride
N-propylbiguanide hydrochloride
N-butylbiguanide hydrochloride
1,1-dimethylbiguanide hydrochloride
1-phenylbiguanide
1,1,3,3-tetramethylguanidine hydrochloride
2-tert-butyl-1,1,3,3-tetramethylguanidine hydrochloride
L-arginine
D-arginine
DL-arginine
arginic acid
N-amidino-N-(2,3-dihydroxypropyl)glycine
N-amidinotaurine
2-imino-1-imidazolidineacetic acid
1-(2,2-diethoxyethyl)guanidine
1H-pyrazole-1-carboxamidine hydrochloride
5-hydroxy-3-methyl-1H-pyrazole-1-carboximidamide
3,5-diamino-1H-1,2,4-triazole-1-carboximidamide hydrochloride
2-guanidone-4-thiazolidone
2-guanidinobenzimidazole
2-guanidinobenzoxazole
2-guanidinobenzothiazole
pyrrolidinoformamidine hydrochloride Among the compounds of formula (III) that may especially be mentioned are the following particularly preferred compounds:
guanidine hydrochloride
guanidine acetate
guanidine sulfate
guanidine carbonate
guanidine bicarbonate
guanidine phosphate
guanidine sulfamate
aminoguanidine hydrochloride
aminoguanidine sulfate
aminoguanidine bicarbonate
1,3-diaminoguanidine hydrochloride
guanylurea phosphate
1-methylguanidine hydrochloride
1,1-dimethylguanidine hydrochloride
1-ethylguanidine hydrochloride
creatine monohydrate
creatinine hydrochloride
agmatine
agmatine sulfate
guanidinoacetic acid
guanidinosuccinic acid
3-guanidinopropionic acid
beta-N-methylguanidinopropionic acid
N-methylguanidinopropionic acid N-(2-hydroxyethyl)guanidine
N-(3-hydroxypropyl)guanidine
biguanide hydrochloride
N-methylbiguanide hydrochloride
N-ethylbiguanide hydrochloride
1,1-dimethylbiguanide hydrochloride
1,1,3,3-tetramethylguanidine hydrochloride
2-tert-butyl-1,1,3,3-tetramethylguanidine hydrochloride
L-arginine
DL-arginine
arginic acid
N-amidino-N-(2,3-dihydroxypropyl)glycine
N-amidinotaurine
2-imino-1-imidazolidineacetic acid
1H-pyrazole-1-carboxamidine hydrochloride
3,5-diamino-1H-1,2,4-triazole-1-carboximidamide hydrochloride
2-guanidone-4-thiazolidone In the compositions according to the invention, the urea of formula (I) or (II) or the guanidine of formula (III) is advantageously present in a molar concentration of between 1M and 8M and more advantageously at a concentration of between 2M and 8M. Of course, any combination of two or more active agents can be used in combination herein.

The pH of the compositions according to the invention is preferably between 3 and 10 and more particularly between 5 and 9.

Advantageously, in the compositions of the invention, the urea of formula (I) or (II) or the guanidine of formula (III) is the sole relaxing active agent.

The compositions according to the invention are preferably either in the form of an aqueous solution or in the form of a thickened cream so as to keep the hair as straight as possible. These creams are preferably made in the form of "heavy" emulsions.

For the purpose of improving the cosmetic properties of keratin fibres or alternatively of attenuating or avoiding their degradation, the composition used according to the invention may also comprise one or more additional cosmetic active agents.

Generally, the additional cosmetic active agent(s) represent(s) from 0.01% to 30% and preferably from 0.1% to 10% by weight relative to the total weight of the cosmetic composition.

Generally, the composition applied to the keratin fibres is applied at a rate of from 0.05 to 20 g and preferably from 0.1 to 10 g of composition per gram of dry keratin fibre.

In a preferred embodiment, after applying the composition, and before raising the temperature of the keratin fibres using a heater or heating means, the composition may be left to stand on the fibres, generally for between 30 seconds and 60 minutes and preferably 5 to 45 minutes.

The process according to the invention comprises, preferably after applying the composition, raising the temperature of the keratin fibres to a temperature of between 110° C. and 250° C.

Advantageously, an iron is used as a heater or heating means.

For the purposes of the present invention, the term "iron" means a device for heating keratin fibres by placing the fibres and the heating device in contact.

The end of the iron that comes into contact with the hair generally has two flat surfaces. These two flat surfaces may be metallic. They may be smooth or notched.

As examples of irons that may be used in the process according to the invention, mention may preferably be made of any type of flat iron and in particular, in a non-limiting manner, those described in U.S. Pat. No. 5,957,140 and U.S. Pat. No. 5,046,516.

The application of the iron may be performed by successive touches separated by a few seconds, or by gradual moving or sliding along locks, etc.

Preferably, the application of the iron in the process according to the invention is performed by continuous movement from the root to the end, in one or more passes.

The process according to the invention may also comprise partial predrying of the keratin fibres before raising the temperature, so as to avoid substantial release of steam that might burn the hands of the hairstylist and the individual's scalp. This predrying step may be performed, for example, using a hairdryer, a drying hood or by free drying.

EXAMPLES

The invention will be understood more clearly with the aid of the non-limiting examples that follow, which constitute preferred embodiments of the invention.

Example 1

A simplified relaxing composition containing urea, at a concentration of 8M in water, as relaxing active agent is prepared. The pH of the composition is 8.06. This composition is applied to naturally frizzy African hair for 15 minutes at a temperature of 40° C. and the hair is then rapidly wiped with a towel.

The hair is then straightened lock by lock using a flat iron heated to 180° C. for 5 to 10 seconds. The hair is efficiently relaxed and feels soft.

Example 2

A simplified relaxing composition containing urea, at a concentration of 4M in water, as relaxing active agent is prepared. The pH of the composition is 7.7. This composition is applied to naturally frizzy African hair for 25 minutes at a temperature of 40° C. and the hair is then rapidly wiped with a towel.

The hair is then straightened lock by lock using a flat iron heated to 180° C., for 5 to 10 seconds. The hair is efficiently relaxed and feels soft.

Example 3

A simplified relaxing composition containing guanidine hydrochloride, at a concentration of 8M in water, as relaxing active agent is prepared. The pH of the composition is 5.46. This composition is applied to naturally frizzy African hair for 15 minutes, at a temperature of 40° C. and the hair is then rapidly wiped with a towel.

The hair is then straightened lock by lock using a flat iron heated to 180° C., for 5 to 10 seconds. The hair is efficiently relaxed and feels soft.

The invention process for relaxing keratin fibres includes hair relaxing, uncurling and straightening, etc. While the invention can be thought of as involving distinct acts, such as (i) applying to the keratin fibres a relaxing composition containing at least one denaturing agent with a molecular mass of greater than 18.1 g/mol, present in a molar concentration of between 1M and 8M, and (ii) raising the temperature of the keratin fibres, using a heater or heating means, to a temperature of between 110 and 250° C., it can also be thought of as a method comprising raising the temperature of keratin fibres, using a heater or heating means, to a temperature of between 110 and 250° C. wherein said keratin fibres comprise on at least a part of a surface thereof at least one denaturing agent with a molecular mass of greater than 18.1 g/mol.

The above written description of the invention provides a manner and process of making and using it such that any person skilled in this art is enabled to make and use the same, this enablement being provided in particular for the subject matter of the appended claims, which make up a part of the original description and including a process for relaxing keratin fibres comprising:

(i) applying to the keratin fibres a relaxing composition comprising, consisting essentially of, or consisting of, at least one denaturing agent with a molecular mass of greater than 18.1 g/mol, present in a molar concentration of between 1M and 8M, and (ii) raising the temperature of the keratin fibres to a temperature of between 110 and 250° C., as well as a method comprising raising the temperature of keratin fibres to a temperature of between 110 and 250° C. wherein said keratin fibres comprise on at least a part of a surface thereof at least one denaturing agent with a molecular mass of greater than 18.1 g/mol.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A process for relaxing human keratin fibres comprising: (i) applying to the keratin fibres a relaxing composition consisting essentially of at least one urea denaturing agent with a molecular mass of greater than 18.1 g/mol, present in a molar concentration of between 1 and 8M, to provide treated keratin fibres, and (ii) raising the temperature of the treated keratin fibres to a temperature of between 110 and 250° C.

2. The process according to claim 1, wherein the relaxing composition comprises between 2 and 8M of the said urea denaturing agent.

3. The process according to claim 1, wherein the temperature is raised to a temperature of between 120 and 220° C.

4. The process according to claim 1, wherein the molar mass of the urea denaturing agent is between 40 and 600 g/mol.

5. The process according to claim 1, wherein the composition is applied to wet keratin fibres.

6. The process according to claim 1, wherein the treated fibres are partially predried prior to raising the temperature of the treated keratin fibres.

7. The process according to claim 1, wherein the at least one urea denaturing agent is represented by formula (I):

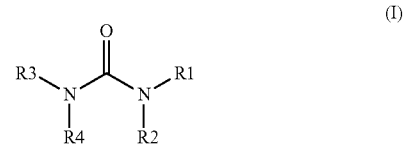

in which: R1, R2, R3 and R4 represent, independently: (v) a hydrogen atom, or (vi) a linear or branched lower C1-C4 alkyl or alkenyl radical, optionally substituted with a radical chosen from: hydroxyl, amino, dimethylamino, carboxyl or carboxamide or N-methylcarboxamide when R1, R2 and R3 represent a hydrogen atom, R4 may also denote a radical chosen from the following: carboxamide; methoxy; ethoxy; 1,2,4-triazolyl; cyclopentyl; methoxycarbonyl; ethoxycarbonyl; CO—CH═CH—COOH; phenyl optionally substituted with a chlorine atom or a hydroxyl radical; benzyl; or 2,5-dioxo-4-imidazolidinyl when R1 and R3 represent a hydrogen atom, R2 may also represent a hydrogen atom or a methyl or ethyl radical and R4 an acetyl radical when R1═R2═H, R3 and R4 may also form, with the nitrogen atom that bears them, a piperidine or 3-methylpyrazole or 3,5-dimethylpyrazole or maleimide ring R1 and R2, and also R3 and R4, may also form, with the nitrogen atom that bears them, an imidazole ring.

8. The process according to claim 1, wherein the at least one urea denaturing agent is represented by formula (II):

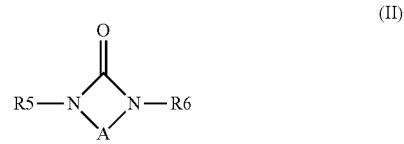

in which: R5 and R6 represent, independently of each other: (iii) a hydrogen atom, or (iv) a linear or branched C1-C4 lower alkyl radical, optionally substituted with a radical chosen from: hydroxyl, amino, dimethylamino, carboxyl or carboxamide, and A represents the radicals: CH2-CH2 or CH═CH or CH2-CO or CO—NH or CH═N or CO—CO or CHOH—CHOH or (HOOC)CH—CH or CHOH—CO or CH2-CH2-CH2 or CH2-NH—CO or CH═C(CH3)-CO or NH—CO—NH or CH2-CH2-CO or CH2-N(CH3)-CH2 or NH—CH2-NH or CO—CH(CH3)-CH2 or CO—CH2-CO or CO—NH—CO or CO—CH(COOH)—CH2 or CO—CH═C(COOH) or CO—CH═C(CH3) or CO—C(NH2)═CH or CO—C(CH3)═N or CO—CH═CH or CO—CH═N or CO—N═CH.

9. The process according to claim 1, wherein the at least one urea denaturing agent is selected from the group consisting of
urea
methylurea
ethylurea
propylurea
isopropylurea
n-butylurea
sec-butylurea
isobutylurea
tert-butylurea
cyclopentylurea
1-ethoxyurea
2-hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleimide
biuret
N-carbamoylmaleamic acid
1-piperidinecarboxamide
1,2,4-triazol-4-ylurea
hydantoic acid
methyl allophanate
ethyl allophanate
acetylurea
2-hydroxyethyleneurea
2-(hydroxyethyl)ethyleneurea
N-allyl-N'-ethylurea
diallylurea
2-chloroethylurea
N,N-dimethylurea
N,N-diethylurea
N,N-dipropylurea
1-cyclopentyl-1-methylurea
1,3-dimethylurea
1,3-diethylurea
1,3-bis(2-hydroxyethyl)urea
1,3-bis(2-hydroxypropyl)urea
1,3-bis(3-hydroxypropyl)urea
1,3-dipropylurea
1-ethyl-3-propylurea
1-sec-butyl-3-methylurea
1-isobutyl-3-methylurea
1-cyclopentyl-3-methylurea
N-acetyl-N'-methylurea
trimethylurea
1-butyl-3,3-dimethylurea
tetramethylurea and
benzylurea.

10. The process according to claim 1, wherein the at least one urea denaturing agent is selected from the group consisting of
parabanic acid
1,2-dihydro-3-H-1,2,4-triazol-2-one
barbituric acid
uracil
1-methyluracil
3-methyluracil
5-methyluracil
1,3-dimethyluracil
5-azauracil
6-azauracil
5-fluorouracil
6-fluorouracil
1,3-dimethyl-5-fluorouracil
5-aminouracil
6-aminouracil
6-amino-1-methyluracil
6-amino-1,3-dimethyluracil
4-chlorouracil
5-chlorouracil
5,6-dihydrouracil
5,6-dihydro-5-methyluracil
2-imidazolidone hydrate
1-methyl-2-imidazolidinone
1,3-dimethyl-2-imidazolidinone
4,5-dihydroxyimidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydantoin
5-n-propylhydantoin
5-ethyl-5-methylhydantoin
5-hydroxy-5-methylhydantoin
5-hydroxymethylhydantoin
1-allylhydantoin
1-aminohydantoin
hydantoin 5-acetic acid
4-amino-1,2,4-triazolone-3,5-dione
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
barbituric acid
1,3-dimethylbarbituric acid
cyanuric acid
1-methylhexahydropyrimidine-2,4-dione
1,3-dimethyl-3,4,5,6-tetrahydro-2-1H-pyrimidinone
5-(hydroxymethyl-2,4-(1H,3H)-pyrimidinedione
2,4-dihydroxypyrimidine-5-carboxylic acid
6-azathymine 5-methyl-1,3,5-triazinan-2-one
N-carbamoylmaleamic acid and
alloxan monohydrate.

11. The process according to claim 1, wherein the temperature of the treated keratin fibres is raised to a temperature of between 110 and 250° C. with a heater.

12. The process according to claim 1, wherein the temperature of the treated keratin fibres is raised to a temperature of between 110 and 250° C. with a heating means.

13. The process according to claim 11, wherein the temperature of the treated keratin fibres is raised to a temperature of between 110 and 250° C. with an iron.

14. The process according to claim 1, wherein said composition is in the form of an aqueous solution or in the form of a thickened cream.

15. The process according to claim 1, wherein the human keratin fibres are hair fibres.

16. A process for relaxing human keratin fibres comprising: (i) applying to the keratin fibres a relaxing composition consisting of at least one urea denaturing agent with a molecular mass of greater than 18.1 g/mol, present in a molar concentration of between 1 and 8M, to provide treated keratin fibres, and (ii) raising the temperature of the treated keratin fibres to a temperature of between 110 and 250° C.

17. A process comprising raising the temperature of keratin fibres to a temperature of between 110 and 250° C., wherein said keratin fibres comprise on at least a part of a surface thereof at least one urea denaturing agent with a molecular mass of greater than 18.1 g/mol.

18. The process according to claim 17, wherein the temperature of the keratin fibres is raised to a temperature of between 110 and 250° C. with an iron.

\* \* \* \* \*